United States Patent
Costello

(10) Patent No.: US 9,498,364 B2
(45) Date of Patent: Nov. 22, 2016

(54) MEDICAL DEVICE DELIVERY SYSTEM AND METHOD OF FLUSHING SAME

(71) Applicant: Cook Medical Technologies LLC, Bloomington, IN (US)

(72) Inventor: Kieran Costello, Cullenagh (IE)

(73) Assignee: Cook Medical Technologies LLC, Bloomington, IN (US)

( * ) Notice: Subject to any disclaimer, the term of this patent is extended or adjusted under 35 U.S.C. 154(b) by 257 days.

(21) Appl. No.: 14/162,012

(22) Filed: Jan. 23, 2014

(65) Prior Publication Data
US 2014/0296960 A1    Oct. 2, 2014

Related U.S. Application Data

(60) Provisional application No. 61/806,430, filed on Mar. 29, 2013.

(51) Int. Cl.
*A61F 2/06* (2013.01)
*A61F 2/966* (2013.01)

(52) U.S. Cl.
CPC ..................................... *A61F 2/966* (2013.01)

(58) Field of Classification Search
CPC ................... A61F 2/966; A61F 2/962; A61F 2002/9517; A61F 2/06
See application file for complete search history.

(56) References Cited

U.S. PATENT DOCUMENTS

| | | | |
|---|---|---|---|
| 5,391,172 A | | 2/1995 | Williams et al. |
| 6,004,328 A | * | 12/1999 | Solar ........................ 623/1.11 |
| 6,860,898 B2 | | 3/2005 | Stack et al. |
| 7,955,370 B2 | | 6/2011 | Gunderson |
| 8,057,529 B2 | | 11/2011 | Cox et al. |
| 8,062,345 B2 | | 11/2011 | Ouellette et al. |
| 8,308,790 B2 | | 11/2012 | Arbefeuille et al. |

* cited by examiner

*Primary Examiner* — Victor Nguyen
(74) *Attorney, Agent, or Firm* — Liell & McNeil

(57) ABSTRACT

A medical device delivery system includes a catheter defining an inner space, and an outer retractable portion positioned over the catheter and defining an annular space between the catheter and the outer retractable portion. At least one bypass opening through a sidewall of the catheter fluidly connects the inner space and the annular space. A tubular sealing member is positioned in the annular space proximal to the bypass opening. The tubular sealing member is movable between a compressed state in which proximal fluid flow through the annular space is inhibited by the tubular sealing member, and a non-compressed state in which proximal fluid flow through the annular space at the tubular sealing member is permitted.

20 Claims, 2 Drawing Sheets

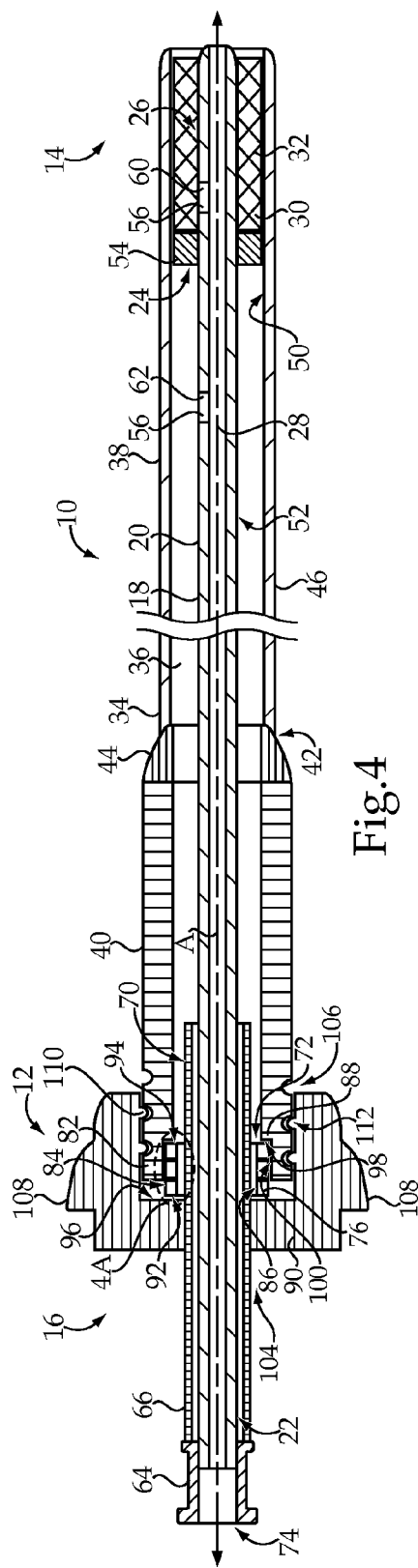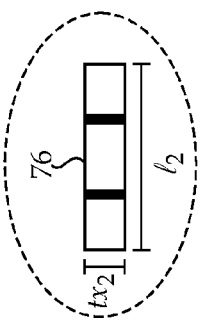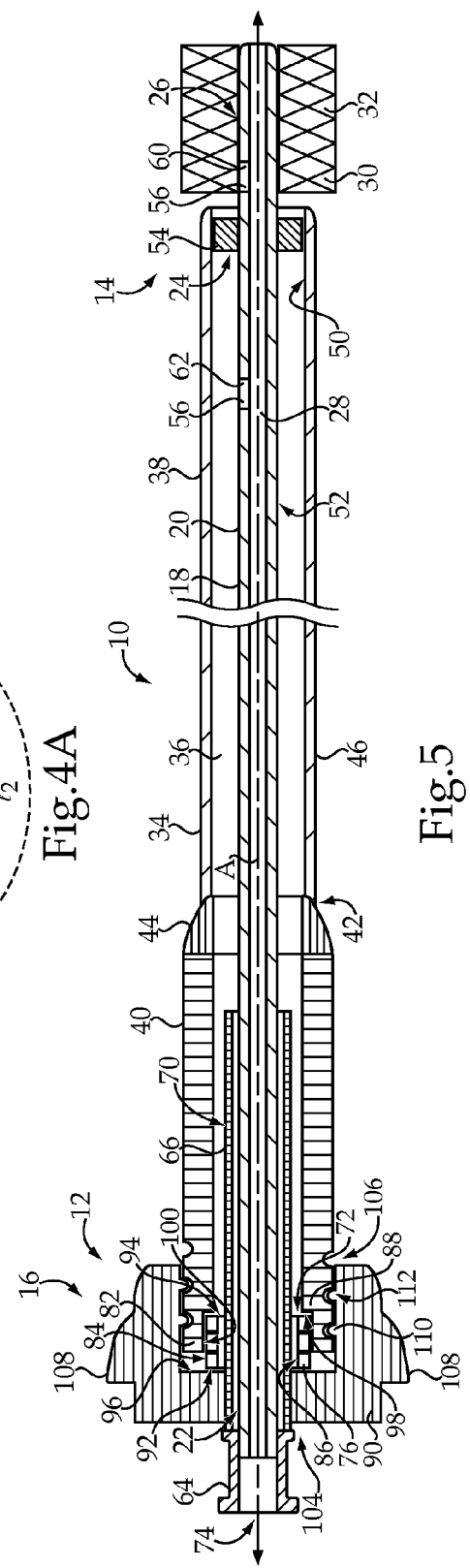

MEDICAL DEVICE DELIVERY SYSTEM AND METHOD OF FLUSHING SAME

TECHNICAL FIELD

The present disclosure relates generally to a medical device delivery system including a catheter defining an inner space and an outer retractable portion positioned over the catheter and defining an annular space, and more particularly to a bypass opening of the catheter fluidly connecting the inner space and the annular space and a tubular sealing member configured to selectively seal the annular space.

BACKGROUND

Various medical devices, including stents, stent grafts, and venous filters, are deployed within the vasculature of a patient using delivery systems. Some of the medical devices are self-expanding, in a radial direction, and require restriction from radial expansion prior to deployment. According to some coaxial delivery systems, an outer sheath maintains a restricted position of the self-expanding medical device during advancement of the medical device to a deployment site. Once the medical device, which is supported on an inner catheter, is positioned at or near the deployment site, the sheath is removed, or refracted, to permit radial expansion of the self-expanding medical device. The retraction of the sheath is typically facilitated through manipulation of a handle positioned at a proximal end of the deployment system.

The interior spaces of the medical device delivery system are typically flushed prior to use to remove air from the medical device delivery system and, thus, reduce the risk of introducing air into the vascular system. With particular regard to coaxial medical device delivery systems, a separate flushing port is typically provided for each lumen, or space, of the coaxial medical device delivery system. For example, the inner catheter defines a first space having a first flushing port, and the outer sheath defines a second space having a second flushing port. To flush the medical device delivery system, a clinician must flush each of the separate spaces independently using a respective one of the respective flushing ports. This conventional arrangement typically utilizes one or more o-ring seals to seal the interior spaces from proximal leakage of the flushing liquid from the medical device delivery system.

U.S. Pat. No. 8,057,529 to Cox et al. teaches a flushing system for a stent delivery system that includes openings extending through an inner tubular member of the stent delivery system. The openings effectively open a passageway from a guide wire lumen defined by the inner tubular member to an annular space formed between the inner tubular member and an outer tubular member of the stent delivery system. A mandrel is placed in the guide wire lumen at a distal tip assembly of the stent delivery system to block the flow of a sterile flushing fluid through the distal tip. Although the Cox et al. reference discusses the potential use of a single flushing port, sealing of the spaces defined by the inner and outer tubular members is not discussed. Further, there remains a continuing need for efficient and effective medical device delivery systems, including improved flushing systems therefor.

The present disclosure is directed toward one or more of the problems or issues set forth above.

SUMMARY OF THE DISCLOSURE

In one aspect, a medical device delivery system includes a catheter defining an inner space, and an outer retractable portion positioned over the catheter and defining an annular space between the catheter and the outer retractable portion. At least one bypass opening through a sidewall of the catheter fluidly connects the inner space and the annular space. A tubular sealing member is positioned in the annular space proximal to the bypass opening. The tubular sealing member is movable between a compressed state in which proximal fluid flow through the annular space is inhibited by the tubular sealing member, and a non-compressed state in which proximal fluid flow through the annular space at the tubular sealing member is permitted.

In another aspect, a method of flushing the medical device delivery system described above is provided. The method includes a step of advancing a flushing liquid from one of the inner space and the annular space to another of the inner space and the annular space through the bypass opening. Proximal flow of the flushing liquid through the annular space is inhibited with the tubular sealing member while the tubular sealing member is in the compressed state. The method also includes moving the tubular sealing member from the compressed state to the non-compressed state.

BRIEF DESCRIPTION OF THE DRAWINGS

FIG. 4 is a sectioned side diagrammatic view of the medical device delivery system of FIG. 1, with the tubular sealing member shown in a non-compressed state;

FIG. 4A is an enlarged view of a portion of the medical device delivery system of FIG. 4 indicated at '4A"; and FIG. 5 is a sectioned side diagrammatic view of the medical device delivery system of FIGS. 1 and 4, with the tubular sealing member shown in a non-compressed state and the outer retractable portion shown in a proximally retracted position.

DETAILED DESCRIPTION

Figure 1:
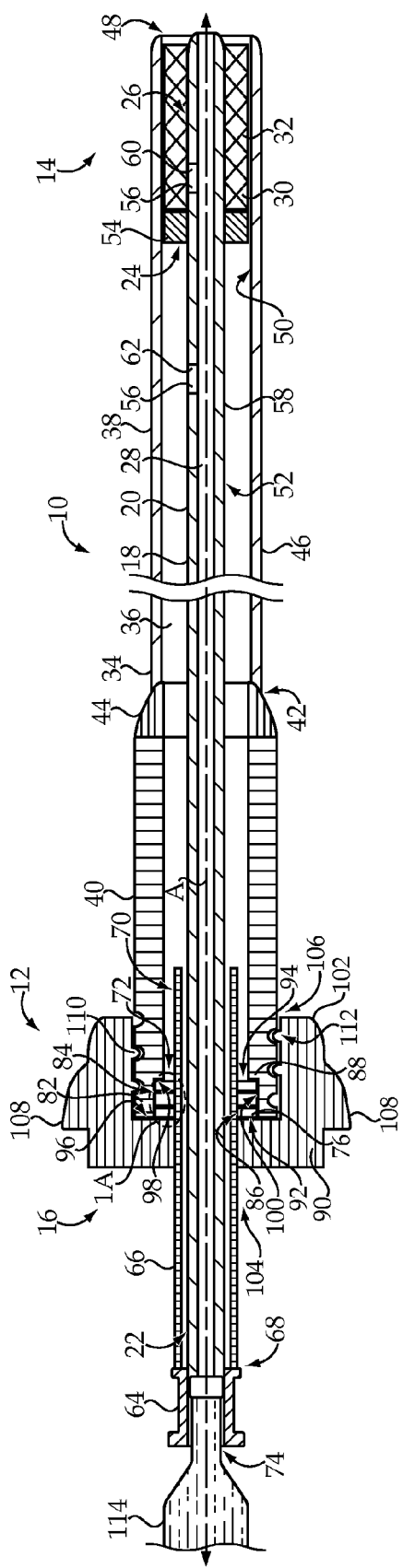
FIG. 1 is a sectioned side diagrammatic view of a medical device delivery system, according to one embodiment of the present disclosure, including a tubular sealing member shown in a compressed state.

Referring to FIG. 1, there is shown a medical device delivery system 10 according to one embodiment of the present disclosure. The medical device delivery system 10 may include a number of components, which may be provided within a sterile, tear open package (not shown), as is known in the art. In performing a medical device delivery procedure on a patient, the components of the medical device delivery system 10 and additional components may be used, depending upon the specifics of the procedure to be performed. As should be appreciated, however, components of the medical device delivery system 10 might be separately packaged and/or the medical device delivery system 10 might also include components in addition to those shown, including components routinely used in percutaneous vascular procedures.

In general, the medical device delivery system 10 has a proximal end 12 and a distal end 14. As shown, a handle assembly 16, which may include relatively rigid components made from medical grade materials, is disposed at the proximal end 12. In the present disclosure, "proximal" will be used to refer to the end of a component or feature that is closest to a clinician, while "distal" is used to refer to a component or feature that is farthest away from the clinician. Such meanings are consistent with conventional use of the terms and, as such, should be understood by those skilled in the art.

According to the exemplary embodiment, the medical device delivery system 10 includes a catheter 18 having an elongate body 20, a proximal end 22, a distal end 24, and a medical device support region 26 at the distal end 24 of the elongate body 20. As shown, the elongate body 20 may be a hollow tubular body defining an inner space, or lumen, 28, and may range in length from several inches to several feet long, and may have a catheter wall diameter that is orders of magnitude smaller than its length. The elongate body 20 may be made from any common medical tube material, such as, for example, a stainless steel, plastic, rubber, silicone, or Teflon material, and may exhibit both firmness and flexibility.

A medical device 30 may be positioned over the catheter 18 at the medical device support region 26. According to the exemplary embodiment, the medical device 30 may include a radially expanding stent 32 for providing tubular support within a blood vessel, canal, duct, or other bodily passageway. Radially expandable stents 32 are known and may be expanded using a balloon, or other known device, positioned at a distal portion of a delivery catheter, such as catheter 18. Alternatively, and according to the exemplary embodiment, the radially expanding stent 32 may be made from a resilient or shape memory material, such as, for example, nitinol, that is capable of self-expanding from a compressed state to an expanded state without the application of a radial force on the stent 32. Such a stent 32 may be referred to as a "self-expanding" stent 32. Although a self-expanding stent 32 will be discussed herein, those skilled in the art should appreciate that the medical device 30 may include alternative radially expandable prosthetic implants. For example, the medical device 30 may include a self-expanding, or otherwise expandable, stent graft or venous filter.

An outer retractable portion 34 of the medical device delivery system 10 may be positioned over the catheter 18 and may define an annular space 36 between the catheter 18 and the outer retractable portion 34. According to the exemplary embodiment, the outer retractable portion 34 may include a retractable sheath 38 and a retractable handle 40 of the handle assembly 16 attached to an open proximal end 42 of the retractable sheath 38, such as via a connector 44. The retractable sheath 38 has an elongate tubular body 46 defining a portion of the annular space 36 extending from the open proximal end 42 to an open distal end 48. As shown, the catheter 18 is telescopically received within the retractable sheath 38. When the self-expanding stent 32, or other medical device, is loaded onto the catheter 18, the self-expanding stent 32 may be restricted from self-expansion using the retractable sheath 38, which is slidably received over the elongate tubular body 20 of the catheter 18. According to this configuration, the retractable sheath 38 restricts radial expansion of the self-expanding stent 32 by contacting the stent 32 with an inner wall surface 50 defining the annular space 36 of the retractable sheath 38. In particular, the medical device 30 is compressed between an outer surface 52 of the catheter 18 and the inner surface 50 of the retractable sheath 38.

According to the exemplary embodiment, a pusher band 54 is also positioned inside the retractable sheath 38 and is located proximal to the medical device 30. In particular, the pusher band 54 may be disposed on the outer surface 52 of the catheter 18 and may be configured to restrict proximal movement of the medical device 30 during relative movement of the catheter 18 and the retractable sheath 38. Pusher bands for use in medical device deployment procedures are generally known and, therefore, will not be discussed herein in greater detail.

At least one bypass opening 56 through a sidewall 58 of the catheter 18 fluidly connects the inner space 28 and the annular space 36. According to the exemplary embodiment, a first bypass opening 60 through the sidewall 58 of the catheter 18 is positioned distal to the pusher band 54, and a second bypass opening 62 through the sidewall 58 of the catheter 18 is positioned proximal to the pusher band 54. Although two bypass openings 56 are shown, any number and/or configuration of bypass openings 56 may be provided, and may be used to flush the inner space 28 and the annular space 36, as will be described below. The bypass openings 56 may be of any desired size and shape and may be formed in any of a number of known ways. For example, the one or more bypass openings 56 may be formed using drilling, punching, skiving, and the like.

The handle assembly 16 may include the retractable handle 40, which is attached to the open proximal end 42 of the retractable sheath 38 and defines a portion of the annular space 36, and a proximal hub 64 and cannula 66 operatively coupled to the proximal end 22 of the catheter 18. According to the exemplary embodiment, the cannula 66 is positioned over the catheter 18 and has a proximal end 68 attached to the proximal hub 64 and a distal end 70 received through a proximal opening 72 of the retractable handle 40. As shown, the proximal end 22 of the catheter 18 may be received within, or otherwise fluidly coupled with, the proximal hub 64. As will be described below, the proximal hub 64 defines a flushing port 74 in fluid communication with both of the inner space 28 and the annular space 36.

Figure 2:
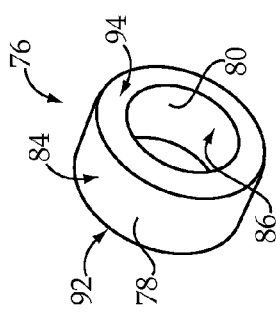
FIG. 2 is a perspective view of the tubular sealing member of the medical device delivery system of FIG. 1.
Figure 1A:
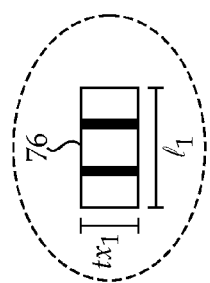
FIG. 1A is an enlarged view of a portion of the medical device delivery system of FIG. 1 indicated at "1A;"

A tubular sealing member 76 is positioned in the annular space 36 proximal to the bypass openings 56. According to some embodiments, at least one bypass opening 56 may be positioned just distal of the tubular sealing member 76 to reduce the potential for air entrapment during a flushing procedure. The tubular sealing member 76 is shown in FIG. 1 in a compressed state in which proximal fluid flow through the annular space 36 is inhibited by the tubular sealing member 76. In this compressed state, and as shown in FIG. 1A, the tubular sealing member 76 has a first axial length $l_1$ and a first radial thickness $tx_1$. The tubular sealing member 76, according to the exemplary embodiment, is shown in perspective in FIG. 2 and may generally include a tubular body 78 defining an opening 80 for receiving the cannula 66 and catheter 18 therethrough. The tubular body 78 may include any known flexible sealing member made from a common sealing material, such as an elastomer, having a generally tubular shape and exhibiting the properties described herein.

According to the exemplary embodiment, the tubular sealing member 76 may be positioned radially between a first portion 82, or flange, of the retractable handle 40 and the cannula 66. In particular, and according to the compressed state, an outer surface 84 of the tubular sealing member 76 may contact the flange 82, and an inner surface 86 of the tubular sealing member 76 may contact the cannula 66. Also, the tubular sealing member 76 may be positioned axially between a second portion 88, or shoulder, of the retractable handle 40 and an actuation device 90. In particular, and according to the compressed state, a first end surface 92 of the tubular sealing member 76 may contact the actuation device 90, and a second end surface 94 of the tubular sealing member 76 may contact the shoulder 88. This relative positioning is described with respect to a longitudinal axis A of the medical device delivery system 10.

According to the compressed state, the actuation device 90 and the retractable handle 40 may be moved toward one another such that the tubular sealing member 76 is axially compressed between an inner surface 96 of the actuation device 90 and a surface 98 defining the shoulder 88 of the retractable handle 40. This axial compression causes the tubular sealing member 76 to be radially expanded into sealing engagement between a surface 100 defining the flange 82 of the retractable handle 40 and the cannula 66. In particular, the inner surface 86 of the tubular sealing member 76 is moved into sealing engagement with the cannula 66 or, more specifically, an outer surface of the cannula 66.

Figure 3:
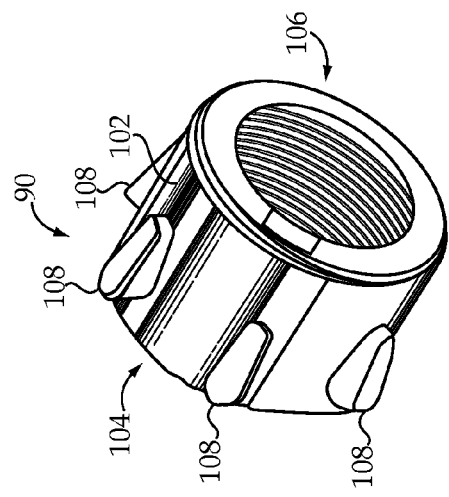
FIG. 3 is a perspective view of the actuation device of FIG. 1.

The actuation device 90 is movable along the longitudinal axis A of the medical device delivery system 10 to move the tubular sealing member 76 into the compressed state. The actuation device 90, an exemplary embodiment of which is shown in FIG. 3, may be in the form of a hollow cap 102 defining a proximal opening 104 sized to receive the cannula 66 and catheter 18 therethrough, and a distal opening 106 sized to be received over the retractable handle 40. The actuation device 90 may include a plurality of projections 108 that permit a clinician to grasp and actuate the actuation device 90. The actuation device 90 may have a threaded engagement with the retractable handle 40. In particular, one or more internal threads 110 of the actuation device 90 may be configured to engage one or more complementary grooves 112 of the retractable handle 40 such that the actuation device 90 may be rotatably received on the retractable handle 40. The threaded engagement may translate rotational movement of the actuation device 90 into axial movement of the actuation device 90 in a known manner.

The actuation device 90 may be proximally retracted relative to the longitudinal axis A to move the tubular sealing member 76 from the compressed state to a non-compressed state, which is shown in FIG. 4. According to the exemplary embodiment, the actuation device 90 may be rotated in one direction to effect proximal movement of the actuation device 90 along the longitudinal axis A and may be rotated another, opposite, direction to effect distal movement along the longitudinal axis A. According to the non-compressed state of the tubular sealing member 76, proximal fluid flow through the annular space 36 at the tubular sealing member 76 is permitted. More particularly, by proximally retracting the actuation device 90, the tubular sealing member 76 is permitted to return to a non-compressed state in which the tubular sealing member 76 has a second axial length $l_2$, as shown in FIG. 4A, that is greater than the first axial length $l_1$ and a second radial thickness $tx_2$ that is less than the first radial thickness $tx_1$. As the radial thickness decreases, the inner surface 86 of the tubular sealing member 76 moves out of sealing engagement, or contact, with the outer surface of the cannula 66.

It should be appreciated that the medical device delivery system 10 presented herein is provided for exemplary purposes only. The structure of various components of the medical device delivery system 10, including the handle assembly 16, tubular sealing member 76, and actuation device 90 may vary greatly according to alternative embodiments.

INDUSTRIAL APPLICABILITY

The present disclosure is generally applicable to medical device delivery systems. Specifically, the present disclosure is applicable to coaxial medical device delivery systems. Such delivery systems may be used to deploy self-expanding medical devices, such as stents, grafts, filters, and the like. More particularly, the present disclosure is applicable to methods and structures for flushing coaxial medical device delivery systems.

Referring generally to FIGS. 1-4, a medical device delivery system 10 includes a catheter 18 defining an inner space 28 and an outer retractable portion 34 positioned over the catheter 18 and defining an annular space 36 between the catheter 18 and the outer retractable portion 34. A medical device 30 may be compressed between an outer surface 52 of the catheter 18 and an inner surface 50 of the outer retractable portion 34 at a distal end 14 of the medical device delivery system 10. The outer retractable portion 34 may include a retractable sheath 38 and a retractable handle 40 of a handle assembly 16 attached to an open proximal end 42 of the retractable sheath 38. The handle assembly 16 may also include a cannula 66 positioned over the catheter 18 and having a proximal end 68 attached to a proximal hub 64 and a distal end 70 received through a proximal opening 72 of the retractable handle 40.

According to the present disclosure, the catheter 18 of the medical device delivery system 10 also includes at least one bypass opening 56 through a sidewall 58 of the catheter 18 to fluidly connect the inner space 28 and the annular space 36. The medical device delivery system 10 also includes a tubular sealing member 76 positioned proximal to the at least one bypass opening 56 for selectively sealing the annular space 36. According to the exemplary embodiment, the tubular sealing member 76 may be positioned radially between a flange 82 of the retractable handle 40 and the cannula 66, and axially between a shoulder 88 of the retractable handle 40 and an actuation device 90. The actuation device 90 may be movable along a longitudinal axis A of the medical device delivery system 10 to move the tubular sealing member 76 between a compressed state, as shown in FIGS. 1 and 1A, and a non-compressed state, as shown in FIGS. 4 and 4A.

Prior to use of the medical device delivery system 10 in a medical device delivery procedure, such as a percutaneous vascular procedure, it may be desirable to flush the medical device delivery system 10. Prior to flushing, a clinician may ensure the tubular sealing member 76 is in the compressed state of FIG. 1. The medical device delivery system 10 may be provided with the tubular sealing member 76 in the compressed state, or the clinician may distally advance the actuation device 90 relative to the longitudinal axis A of the medical device delivery system 10 to move the tubular sealing member 76 from the non-compressed state to the compressed state. For example, the clinician may rotate the actuation device 90 relative to the retractable handle 40, as described above. With the tubular sealing member 76 in the compressed state, the clinician may advance a flushing media, such as saline, from a syringe 114 through the proximal port 74 and into the inner space 28 defined by the catheter 18.

This flushing liquid may then pass from the inner space 28 and into the annular space 36 through the one or more bypass openings 56. The tubular sealing member 76, in the compressed state, inhibits proximal flow of the flushing liquid through the annular space 36 at the tubular sealing member 76. In particular, with the tubular sealing member 76 axially compressed and radially expanded as described above, the tubular sealing member 76 seals the annular space 36 at the tubular sealing member 76 and restricts proximal fluid flow therethrough. The flushing liquid ultimately exits the inner and annular spaces 28 and 36 through the open distal end 14 of the medical device delivery system 10. The compressed state of the tubular sealing member 76 may also function to resist inadvertent deployment of the medical device 30 by frictionally maintaining the catheter 18 stationary with respect to the outer retractable portion 34.

After the medical device delivery system 10 has been flushed, the tubular sealing member 76 may be moved from the compressed state to the non-compressed state of FIGS. 4 and 4A by proximally retracting the actuation device 90 relative to the longitudinal axis A of the medical device delivery system 10. For example, the clinician may rotate the actuation device 90 relative to the retractable handle 40 in a direction opposite the direction required to distally advance the actuation device 90. With the tubular sealing member 76 in the non-compressed state, proximal fluid flow through the annular space 36 at the tubular sealing member 76 is permitted. Specifically, the inner surface 86 of the tubular sealing member 76 is moved out of sealing engagement, or contact, with the cannula 66.

With the tubular sealing member 76 in the non-compressed state, the clinician may proceed with the medical device delivery procedure. For example, with the distal end 14 of the medical device delivery system 10 positioned at a deployment location within a vascular structure of a patient using a known percutaneous vascular access procedure, the medical device 30 may be deployed. In particular, the clinician may slide the retractable sheath 38 with respect to the catheter 18 while maintaining the catheter 18 stationary with respect to the deployment location. For example, to move the medical device delivery system 10 into a deployment configuration, which is shown in FIG. 5, the clinician may maintain a stationary position of the proximal hub 64, while proximally retracting the retractable handle 40 along the cannula 66. The retractable handle 40 and the actuation device 90 are moved toward, and may eventually contact, the proximal hub 64. Since the tubular sealing member 76 is no longer in contact with the cannula 66, no frictional force is provided by the tubular sealing member 76 that would otherwise resist the proximal retraction of the retractable handle 40. With the retractable sheath 38 proximally retracted, as shown, the medical device 30 may be permitted to deploy, such as by expanding in a radial direction.

The medical device delivery system 10 disclosed herein provides an effective means for flushing the inner and annular spaces 28 and 36 of the medical device delivery system 10. In particular, the inner and annular spaces 28 and 36 may be flushed using exactly one flushing port 74. As such, the time required for the flushing procedure may be minimized. Further, requiring flushing through only one port 74 reduces the risk that one of the two ports required for conventional flushing will be forgotten. Further, the medical device delivery system 10 disclosed herein provides for selective sealing of the annular space 36 such that the annular space 36 may be sealed from proximal leakage of the flushing liquid during flushing, but may be moved into a non-compressed state after the flushing has been performed so that the tubular sealing member 76 does not interfere with the medical device deployment. As such, medical device deployments utilizing this feature may be more accurate.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:

1. A medical device delivery system, comprising:
a catheter defining an inner space;
an outer retractable portion positioned over the catheter and defining an annular space between the catheter and the outer retractable portion;
at least one bypass opening through a sidewall of the catheter fluidly connecting the inner space and the annular space; and
a tubular sealing member positioned in the annular space proximal to the bypass opening, wherein the tubular sealing member is movable between a compressed state in which proximal fluid flow through the annular space is inhibited by the tubular sealing member, and a non-compressed state in which proximal fluid flow through the annular space at the tubular sealing member is permitted.

2. The medical device delivery system of claim 1, wherein in the compressed state the tubular sealing member has a first axial length and a first radial thickness, and in the non-compressed state the tubular sealing member has a second axial length that is greater than the first axial length and a second radial thickness that is less than the first radial thickness.

3. The medical device delivery system of claim 2, further including a proximal hub attached at an open proximal end of the catheter, wherein the proximal hub defines a flushing port in fluid communication with both of the inner space and the annular space.

4. The medical device delivery system of claim 3, wherein the outer retractable portion includes a retractable sheath and a retractable handle of a handle assembly attached to an open proximal end of the retractable sheath.

5. The medical device delivery system of claim 4, wherein the handle assembly further includes a cannula positioned over the catheter and having a proximal end attached to the proximal hub and a distal end received through a proximal opening of the retractable handle.

6. The medical device delivery system of claim 5, wherein the tubular sealing member is positioned radially between a first portion of the retractable handle and the cannula, and the tubular sealing member is positioned axially between a second portion of the retractable handle and an actuation device.

7. The medical device delivery system of claim 6, wherein the actuation device is movable along a longitudinal axis of the medical device delivery system to move the tubular sealing member between the compressed state and the non-compressed state.

8. The medical device delivery system of claim 7, wherein the actuation device has a threaded engagement with the retractable handle, wherein the threaded engagement translates rotational movement of the actuation device into axial movement of the actuation device.

9. The medical device delivery system of claim 1, further including a medical device compressed between an outer surface of the catheter and an inner surface of the outer retractable portion.

10. The medical device delivery system of claim 9, wherein the medical device is a self-expanding stent.

11. The medical device delivery system of claim 9, further including a pusher band disposed on the outer surface of the catheter proximal to the medical device and configured to restrict proximal movement of the medical device during relative movement of the catheter and the outer retractable portion.

12. A medical device delivery system, comprising:
a catheter defining an inner space;
an outer retractable portion positioned over the catheter and defining an annular space between the catheter and the outer retractable portion;
at least one bypass opening through a sidewall of the catheter fluidly connecting the inner space and the annular space; and
a tubular sealing member positioned in the annular space proximal to the bypass opening, wherein the tubular sealing member is movable between a compressed state in which proximal fluid flow through the annular space is inhibited by the tubular sealing member, and a non-compressed state in which proximal fluid flow through the annular space at the tubular sealing member is permitted; and
the at least one bypass opening includes a first bypass opening through the sidewall of the catheter distal to the pusher band and a second bypass opening through the sidewall of the catheter proximal to the pusher band.

13. A method of flushing a medical device delivery system, the medical device delivery system including a catheter defining an inner space, an outer retractable portion positioned over the catheter and defining an annular space between the catheter and the outer retractable portion, at least one bypass opening through a sidewall of the catheter fluidly connecting the inner space and the annular space, and a tubular sealing member positioned in the annular space proximal to the bypass opening, wherein the tubular sealing member is movable between a compressed state in which proximal fluid flow through the annular space is inhibited by the tubular sealing member, and a non-compressed state in which proximal fluid flow through the annular space at the tubular sealing member is permitted, the method comprising steps of:
advancing a flushing liquid from one of the inner space and the annular space to another of the inner space and the annular space through the bypass opening;
inhibiting proximal flow of the flushing liquid through the annular space with the tubular sealing member while the tubular sealing member is in the compressed state; and
moving the tubular sealing member from the compressed state to the non-compressed state in which proximal fluid flow through the annular space at the tubular sealing member is permitted.

14. The method of claim 13, wherein the inhibiting step includes inhibiting proximal flow of the flushing liquid through the annular space by axially compressing and radially expanding the tubular sealing member.

15. The method of claim 13, further including introducing the flushing liquid into the inner space and the annular space through exactly one flushing port.

16. The method of claim 13, wherein the advancing step includes advancing the flushing liquid sequentially through a proximal hub attached at an open proximal end of the catheter, through the inner space, through the bypass opening, and through the annular space.

17. The method of claim 13, wherein the moving step further includes rotating an actuation mechanism.

18. The method of claim 17, wherein the moving step further includes translating rotational movement of the actuation mechanism into axial movement of the actuation mechanism using a threaded engagement between the actuation mechanism and a retractable handle.

19. The method of claim 17, further including compressing a medical device between an outer surface of the catheter and an inner surface of the outer retractable portion.

20. The method of claim 19, further including:
proximally retracting the outer retractable portion using the retractable handle while the tubular sealing member is in a compressed state; and
radially expanding the medical device responsive to the proximally retracting step.

* * * * *